United States Patent [19]

Goldberg

[11] Patent Number: 5,069,898

[45] Date of Patent: Dec. 3, 1991

[54] HAIR ENRICHMENT COMPOSITION AND METHOD OF USE

[75] Inventor: Marvin E. Goldberg, Marlboro, N.J.

[73] Assignee: Revlon, Inc., New York, N.Y.

[21] Appl. No.: 342,290

[22] Filed: Apr. 24, 1989

[51] Int. Cl.⁵ .......................... A61K 7/06; A61K 7/08
[52] U.S. Cl. .................................. 424/70; 424/195.1; 424/196.1; 514/773; 514/777; 514/782; 514/783; 514/880; 514/929
[58] Field of Search ...................... 424/70, 78, 80, 74, 424/195.1, 196.1; 252/DIG. 13; 514/772, 773, 777, 783, 784, 929, 880

[56] References Cited

U.S. PATENT DOCUMENTS

| | | | |
|---|---|---|---|
| 454,401 | 6/1891 | Fraser | 424/70 |
| 4,460,488 | 7/1984 | Grollier et al. | 252/89.1 |
| 4,508,707 | 4/1985 | Ayukawa | 424/70 |
| 4,565,698 | 1/1986 | Yoshizumi et al. | 424/93 |
| 4,567,039 | 1/1986 | Stadnick et al. | 424/70 |
| 4,584,191 | 4/1986 | Hostettler et al. | 424/70 |
| 4,678,598 | 7/1987 | Ogino et al. | 252/174.17 |
| 4,705,681 | 11/1987 | Maes et al. | 424/70 |
| 4,713,397 | 12/1987 | Hirama et al. | 514/690 |
| 4,745,103 | 5/1988 | Oono | 514/880 |
| 4,885,159 | 12/1989 | Miyake et al. | 424/70 |

FOREIGN PATENT DOCUMENTS

| | | |
|---|---|---|
| 0100915 | 7/1983 | European Pat. Off. |
| 0129197 | 12/1984 | European Pat. Off. |
| 0182756 | 5/1986 | European Pat. Off. |

OTHER PUBLICATIONS

"Cosmetics—Science and Technology," 2nd Ed., vol. 2, John Wiley & Sons, New York, NY, 1972, pp. 345–352.

*Primary Examiner*—Thurman K. Page
*Assistant Examiner*—Amy Hulina
*Attorney, Agent, or Firm*—Julie Blackburn

[57] ABSTRACT

This invention provides a hair enrichment composition which includes a hair-sorbable bulking agent, a blood vessel dilator, and a scalp stimulant, together with a method of using the composition.

9 Claims, No Drawings

HAIR ENRICHMENT COMPOSITION AND METHOD OF USE

This invention is in the field of body-treating compositions, especially live hair and scalp-treating compositions. More particularly, the invention is directed to non-therapeutic products and processes for stimulating the scalp, enriching the hair, and producing an attractive coiffure.

BACKGROUND OF THE INVENTION

It is well known that hair is degraded by a number of environmental factors, such as sunlight and temperature extremes, factors which tend to dehydrate the hair, make it brittle, and cause the hair shafts to split or break. In addition, the hair may be degraded by waving it, bleaching or dyeing it, and also by abrading it while combing, toweling, etc. The resultant degradation manifests itself in disruption of the protective cuticle of the hair shafts, exposing the more vulnerable cortex. The observable result is dull, lifeless hair, lacking natural lubricity and luster, hair which is difficult to comb and style appealingly. Furthermore, the same factors which affect the hair shafts may also affect the scalp in such a way that growth of new hair is retarded.

The aforesaid problems are not new, and a number of cosmetic preparations, such as rinses, tonics, and hair conditioners in the form of aqueous or alcoholic solutions, or heterogeneous lotions and creams, have appeared over the years in attempts to alleviate the effects of such degradation. A number of such products are described, for example, in "Cosmetics—Science and Technology," 2nd Ed., Vol. 2, John Wiley & Sons, New York, N.Y., 1972, esp. pp 345-352.

In general, the hair conditions described in the past incorporate materials which are substantive to the hair or coat the hair shafts with a protective film; that is, materials which are sorbed onto or into the hair shafts and are not washed out easily, but which have a more or less longlasting effect. Once so sorbed, these materials restore lubricity to the hair and increase the diameter of the shafts, making the hair appear fuller, bulkier and easier to manage.

For example, U.S. Pat. No. 4,567,039 discloses a hair conditioning composition which incorporates an organosilicon quaternary ammonium halide which, in alkali, is shown to be substantive to the hair in that it cannot be washed off the hair readily. However, the organosilicon compound is unstable in alkaline solution, so the composition has a short shelf life and must be constituted just prior to use.

U.S. Pat. No. 4,584,191 described hair/skin care compositions containing lower alkyl esters of biotin, vitamin H. These esters are said to be sorbed by the hair and skin more effectively than biotin itself and then converted into biotin in vivo. Biotin is known to be a growth factor present in minute amounts in every living cell.

Hair conditioner formulations containing a prescribed ratio of d-panthenol and d-panthenyl ethyl ether are disclosed in U.S. Pat. No. 4,705,681. Such formulations, when applied to hair, are said to decrease the friction between individual shafts and thereby lessen the abrasion damage when the hair is combed or brushed.

Whereas the hair treatment and conditioning compositions of the prior art are directed to ameliorating the damage done to hair by the environmental and other factors mentioned above, there is a need for new and more effective hair enrichment agents, especially hair enrichment compositions which address the damage caused by the aforesaid factors, not only to the hair shafts, but also to the scalp.

Thus, it is one object of this invention to provide a one-part hair enrichment composition which is stable and exhibits good shelf life. It is another object to provide a hair conditioning composition which not only treats the damaged shafts of hair, but which also enriches and invigorates the scalp.

SUMMARY OF THE INVENTION

Accordingly, this invention provides a hair enrichment composition which includes cosmetically effective amounts of a hair-sorbable bulking agent, a blood vessel dilator, and a scalp stimulant, all contained in a cosmetically acceptable carrier. In preferred embodiments, the bulking agent includes both hair-absorbable and hair-adsorbable components. The blood vessel dilator may incorporate a rubefacient, and the scalp stimulant preferably includes an antipruritic agent. The invention also includes a method for using the new composition in a manner which optimizes its effectiveness.

DETAILED DESCRIPTION

The hair enrichment compositions of this invention incorporate a bulking agent. The bulking agent is sorbable onto or into the shafts of the hair, moderates the damage environmental or other factors may have caused, and increases the diameter of the hair shafts. The bulking agent remains with the hair a reasonable length of time to minimize future damage. The bulking agent may comprise materials set forth in the prior art, such as biotin or an ester thereof, panthenol, or a panthenyl ether, or mixtures thereof. It is preferred that the bulking agent include both hair-absorbable and hair-adsorbable components. The former may be viewed as shaft repair elements, the latter as shaft protective elements. Certain of the preferred bulking agents are believed to function in both roles, however. The bulking agent will comprise a cosmetically effective amount, generally about 0.005 to about 15 percent by weight of the composition.

Although a number of substantive agents believed to be hair-absorbable are known, it is especially preferred that the hair-absorbable bulking agent include some or all of biotin, panthenol, glycoprotein, and mucopolysaccharide. Biotin and panthenol are known to be useful for this purpose. The glycoprotein, containing amino acid residues bound to oligosaccharides, promotes soft, flexible, moisture-retentive films that increase the hair's gloss and the hair shaft diameter. The mucopolysaccharide is a very effective emollient. These components individually may be present in cosmetically effective amounts ranging from about 0.0005 to about 5 percent by weight of the composition. A useful combination includes panthenol, biotin and mucopolysaccharide, about 0.25-15 percent by weight in the aggregate being especially useful.

The hair-adsorbable component of the bulking agent is advantageously a cosmetically acceptable film-forming polymer or mixture thereof. Such materials include, for example, polyvinylpyrrolidone and copolymers or derivatives thereof; for example, copolymers with the ethyl or butyl ester of PVA/MA (partially neutralized), copolymers with vinyl acetate/crotonic acid, copolymers of PVP/VA in all proportions, Polyquaternium-11, and copolymers with ethyl methacrylate/oleyl methacrylate/diethylaminoethyl methacrylate quaternized with dimethyl sulfate, as well as carboxyvinyl polymers, such as hydroxyethyl cellulose, hydroxypropyl methylcellulose, and guar gum, zanthan gum, tragacanth gum, and other natural viscosity boosters. In addition to its film-forming protective and hair bulking functions, a carboxyvinyl polymer can also be utilized to control the viscosity of the composition through pH adjustment; amines and ammonium hydroxide are useful in this regard, for example.

In addition, various film-modifying agents may be present. These include, for example, various protein-derived materials such as adenosine triphosphate and protein hydrolysates, i.e., keratin, silk, elastin, and collagen, as well as polypeptides, amino acid mixtures, or a condensation reaction product of hydrolyzed animal protein. The hair-adsorbable component of the bulking agent may be present in the composition in cosmetically effective amount, about 0.003 to about 15 percent by weight, each individual element being employed at about 0.001 to about 5 percent by weight.

In addition to a hair-sorbable bulking agent, the hair enrichment compositions of this invention include a blood vessel dilator. In this regard, a number of substances with known rubefacient efficacy can be employed. These include, for example, chloral hydrate, formic acid spirits, quinine and its salts, tincture of cantharides, tincture of capsicum, tincture of cinchona, as well as cade, pine, and birch tars. It is preferred, however, that the dilator incorporate a derivative of nicotinic acid, preferably an ester, such as a lower alkyl, e.g., methyl or ethyl, nicotinate. An especially useful dilator is vitamin E nicotinate. The dilator will be present in the composition in a cosmetically effective amount in the range of about 0.001 to about 5 percent by weight.

Finally, the hair enrichment compositions should include a scalp stimulant. Such stimulants include cosmetically acceptable alcohols, such as ethanol, isopropanol, and combinations thereof. Suitable stimulants also include antipruritic agents. Such agents may provide a cooling sensation, like menthol, or a warming sensation, like camphor, for example. It is preferred that both be present in the composition. The scalp stimulant agent will constitute a cosmetically effective amount, generally about 0.002 to about 10 percent by weight of the composition.

The hair enrichment compositions of this invention also include a cosmetically acceptable carrier for the ingredients described above. Although either water or mixtures of water with lower alkyl alcohols may be utilized, it is preferred that the composition not include the alcohol. Various surface-active agents, fragrances and preservatives may also be present in the carrier.

Having described the hair enrichment compositions of this invention in general, the following specific example will clarify the nature of the compositions.

EXAMPLE

| Ingredient | Parts by Weight |
| --- | --- |
| Panthenol | 0.1 |
| Biotin | 0.0005 |
| Glycoprotein | 0.1 |
| Mucopolysaccharide | 0.01 |
| Carboxyvinyl polymer | 0.05 |
| Ammonium hydroxide (28%) | 0.014 |
| Polyvinylpyrrolidone | 0.125 |
| Adenosine triphosphate | 0.01 |
| Vitamin E nicotinate | 0.01 |

| Ingredient | Parts by Weight |
| --- | --- |
| Camphor | 0.1 |
| Menthol | 0.1 |
| Nonoxynol-12 | 0.2 |
| Dimethylhydantoin | 0.4 |
| Water q.s. | 100.0 |

All of the aforesaid ingredients are available commercially. The glycoprotein is Glyprosol 20, available from Brooks Industries, Inc., South Plainfield, N.J. The carboxyvinyl polymer is a Carbopol (registered trademark of BF Goodrich Co.) resin, Type 941. The polyvinylpyrrolidone is available from BASF or GAF, for example, in various molecular weights, the higher molecular weights, e.g., $10^6$ being preferred.

In preparing the exemplified composition it is preferable to dissolve the panthenol, PVP and water separately and then add that solution to the other ingredients prior to adding the dimethylhydantoin and mixing until uniform.

The hair enrichment compositions of this invention are using by applying to the freshly washed head an amount of the composition sufficient to enrich the hair and scalp (e.g. about 1/30 to about ¼ oz. of the exemplified composition), and the massaging the composition into the scalp for a period of time sufficient to cause such enrichment (e.g., about 60 sec. for the exemplified composition), rinsing the hair with plain water, and then drying it.

What is claimed is:

1. An aqueous-based hair enrichment composition which is effective in restoring damaged shafts of hair and invigorating the scalp comprising, as a cosmetically acceptable carrier, a major amount of water and, in cosmetically effective amounts:

about 0.005 to about 15 wt % of hair sorbable bulking agent, comprising panthenol, biotin, mucopolysaccharides or mixtures thereof, about 0.001 to about 5 wt % of a scalp blood vessel dilator which is a rubefacient selected from the group consisting of vitamin E nitcotinate, chloral hydrate, formic acid spirits, quinine, quinine salts, tincture of cantharides, tincture of cinchona, tincture of capsicum, cade tar, pine tar, and birch tar, and about 0.002 to about 10 wt % of a scalp stimulant selected from cosmetically acceptable alcohols and antipruritic agents.

2. The composition of claim 1 wherein said blood vessel dilator includes vitamin E nicotinate.

3. The composition of claim 1 wherein said scalp stimulant includes antipruritic agents providing both a feeling of warmth and an aura of coolness.

4. The composition of claim 1 wherein said cosmetically acceptable carrier is substantially free of lower alkyl alcohol.

5. A hair enrichment composition comprising cosmetically effective amounts of a hair-sorbable bulking agent which includes panthenol, biotin, glycoprotein, mucopolysaccharide, carboxyvinyl polymer, and vinylpyrrolidonyl polymer, a vitamin E nicotinate, and a scalp stimulant which includes camphor and menthol, all combined in a cosmetically acceptable aqueous carrier.

6. A method for enriching the hair and scalp which comprises
   applying to the hair and scalp a composition according to claim 1 in an amount to enrich the hair and scalp,
   massaging said composition into the scalp for a time sufficient to cause such enrichment, and then rinsing the hair with water and drying it.

7. A method for enriching the hair and scalp which comprises
   applying to the hair and scalp a composition according to claim 1 in an amount to enrich the hair and scalp,
   massaging said composition into the scalp for a time sufficient to cause such enrichment, and then rinsing the hair with water and drying it.

8. A hair enrichment composition comprising cosmetically effective amounts of
   hair-sorbable bulking agent consisting essentially of a mixture of panthenol, biotin, and mucopolysaccharide,
   a scalp blood vessel dilator which is a rubefacient selected from the group consisting of vitamin E nicotinate, chloral hydrate, formic acid spirits, quinine, quinine salts, tincture of cantharides, tincture of cinchona, tincture capsicum, cade tar, pine tar, and birch tar, and
   a scalp stimulant selected from cosmetically acceptable alcohols and antipruritic agents, all combined in a cosmetically acceptable carrier.

9. A hair enrichment composition comprising cosmetically effective amounts of
   hair-sorbable bulking agent which includes a hair-absorbable component and a hair-adsorbable component which is a film-forming polymer selected from carboxyvinyl and polyvinylpyrolidinyl polymers,
   a scalp blood vessel dilator which is a rubefacient selected from the group consisting of vitamin E nicotinate, chloral hydrate, formic acid spirits, quinine, quinine salts, tincture of cantharides, tincture of cinchona, tincture capsicum, cade tar, pine tar, and birch tar, and
   a scalp stimulant selected from cosmetically acceptable alcohols and antipruritic agents, all combined in a cosmetically acceptable carrier.

* * * * *